US006679249B2

(12) United States Patent
Addington et al.

(10) Patent No.: US 6,679,249 B2
(45) Date of Patent: Jan. 20, 2004

(54) APPARATUS FOR TREATMENT OF CHRONIC OBSTRUCTIVE PULMONARY DISEASE AND ASSOCIATED METHOD

(75) Inventors: W. Robert Addington, Melbourne Beach, FL (US); Robert E. Stephens, Kansas City, MO (US); Stuart P. Miller, Melbourne Beach, FL (US)

(73) Assignee: Pneumoflex Systems, L.L.C., Melbourne Beach, FL (US)

( * ) Notice: Subject to any disclaimer, the term of this patent is extended or adjusted under 35 U.S.C. 154(b) by 237 days.

(21) Appl. No.: 09/943,494

(22) Filed: Aug. 30, 2001

(65) Prior Publication Data

US 2002/0100476 A1 Aug. 1, 2002

Related U.S. Application Data

(60) Continuation-in-part of application No. 09/442,658, filed on Nov. 18, 1999, which is a division of application No. 09/064,028, filed on Apr. 21, 1998, now Pat. No. 6,004,268.
(60) Provisional application No. 60/229,066, filed on Aug. 30, 2000.

(51) Int. Cl.$^7$ .............................................. A61M 11/00

(52) U.S. Cl. ........................... 128/200.14; 128/200.16; 128/203.12

(58) Field of Search ....................... 128/200.14, 200.16, 128/200.18, 203.12, 200.24

(56) References Cited

U.S. PATENT DOCUMENTS

| | | | | |
|---|---|---|---|---|
| 2,918,917 A | * | 12/1959 | Emerson | 128/205.19 |
| 3,565,072 A | * | 2/1971 | Gauthier | 128/200.16 |
| 3,745,991 A | * | 7/1973 | Gauthier et al. | 600/529 |
| 3,812,854 A | * | 5/1974 | Michaels et al. | 128/200.16 |
| 4,106,503 A | * | 8/1978 | Rosenthal et al. | 128/200.18 |
| 4,257,415 A | * | 3/1981 | Rubin | 128/200.21 |
| 4,907,581 A | * | 3/1990 | King | 128/200.18 |

(List continued on next page.)

FOREIGN PATENT DOCUMENTS

| | | |
|---|---|---|
| WO | WO 99 36115 A | 7/1999 |
| WO | WO 99 49917 A | 10/1999 |

OTHER PUBLICATIONS

Addington, W. Robert, D.O.; Stephens, Robert E., Ph.D.; Widdicombe, John G., D.M.; Anderson, Jeffrey W., D.O., ; Rekab, Kamel, Ph.D., *The Effect Of Tartaric Acid–Induced Cough On Pulmonary Function In Normal And Asthmatic Humans*, PFT in Normal and Asthmatic Humans European Respiratory, Jul. 3, 2001.

Fujimura M et al : *Sex Difference In The Inhaled Tartaric Acid Cough Threshold In Non–Atopic Healthy Subjects*, Thorax, London, GB, vol. 45, No. 8, Aug. 1990, pp. 633–634.

Charles E. Lapple; *Atomization*, pp. 260–264.

*Primary Examiner*—Aaron J. Lewis
(74) *Attorney, Agent, or Firm*—Allen, Dyer, Doppelt, Milbrath & Gilchrist, P.A.

(57) ABSTRACT

An apparatus and method for treatment of a patient having a pulmonary disease involving chronic obstruction of the airways includes a container having therein a chamber containing a composition of L-tartrate in a pharmaceutically acceptable carrier; an opening connected to the chamber so as to provide an outlet therefor, the opening sized for producing droplets of a predetermined size range responsive to the composition being motivated from the chamber through the opening; and a source of motivating force connected with the chamber so as to motivate the composition through the opening to thereby cause nebulization of the composition. A treatment kit comprises the container described and a mouthpiece connectable to the container so as to be in fluid connection with the opening and downstream therefrom to thereby convey the nebulized composition into a patient's mouth to thereby facilitate oral inhalation of the nebulized composition by the patient.

8 Claims, 3 Drawing Sheets

U.S. PATENT DOCUMENTS

| | | | | |
|---|---|---|---|---|
| 5,233,975 | A | * 8/1993 | Choate | 128/200.14 |
| 5,372,126 | A | * 12/1994 | Blau | 128/200.14 |
| 5,678,563 | A | * 10/1997 | Addington et al. | 600/529 |
| 5,767,068 | A | * 6/1998 | VanDevanter et al. | 514/9 |
| 5,839,430 | A | 11/1998 | Cama | |
| 6,004,268 | A | * 12/1999 | Addington et al. | 600/300 |
| 6,058,932 | A | * 5/2000 | Hughes | 128/200.24 |
| 6,161,536 | A | * 12/2000 | Redmon et al. | 128/200.14 |
| 6,283,118 | B1 | * 9/2001 | Lu | 128/200.16 |

OTHER PUBLICATIONS

Richard A. Matthay and Alejandro C. Arroliga; *Chronic Airways Diseases*, Cecil Textbook Of Medicine, 20th Edition, vol. 1, pp. 381–389; W. B. Saunders Company, A Division of Harcourt Brace & Company.

Braunwald, Isselbacher, Petersdorf, Wilson, Martin, Fauci; *Disorders Of The Respiratory System*, Harrison's Principles Of Internal Medicine, 11th Edition, Chapter 202 (one page).

* cited by examiner

APPARATUS FOR TREATMENT OF CHRONIC OBSTRUCTIVE PULMONARY DISEASE AND ASSOCIATED METHOD

RELATED APPLICATION

This application is a continuation-in-part of and claims priority from copending application Ser. No. 09/442,658 filed on Nov. 18, 1999, which is a division of Ser. No. 09/064,028 filed on Apr. 21, 1998 and which resulted in U. S. Pat. No. 6,004,268 issued on Dec. 21, 1999; this application also claims priority from co-pending U.S. Provisional Application Ser. No. 60/229,066 which was filed on Aug. 30, 2000; all priority applications being incorporated herein by reference in their entirety.

FIELD OF THE INVENTION

The present invention relates to the medical field, and more particularly to a treatment for a pulmonary disease involving chronic obstruction of the airways, to a nebulizer apparatus for delivery of the medication, and to a treatment kit therefor.

REFERENCES CITED

1. Addington W R, Stephens R E, Gilliland K, Rodriguez M. Assessing the laryngeal cough reflex and the risk of developing pneumonia after stroke. Arch Phys Med Rehabil. 1999;80:150–4.
2. Addington W R, Stephens R E, Gilliland K A. Assessing the laryngeal cough reflex and the risk of developing pneumonia after stroke: an interhospital comparison. Stroke. 1999;30:1203–7.
3. Tomori Z, Stransky A. Electroneurographic and pneumotachographic analysis of the expiration reflex. Physiol Bohemoslov. 1973;22:589–601.
4. Fujimura M, Sakamoto S, Kamio Y, Matsuda T. Cough receptor sensitivity and bronchial responsiveness in normal and asthmatic subjects. Eur Respir J. 1992;5:291–5.
5. Fujimura M, Sakamoto S, Kamio Y, Saito M, Miyake Y, Yasui M, Matsuda T. Cough threshold to inhaled tartaric acid and bronchial responsiveness to methacholine in patients with asthma and sino-bronchial syndrome. Intern Med. 1992;31:17–21.
6. Addington W R, Stephens R E, Ockey R R, Kann D, Rodriguez M. A new aspiration screening test to assess the need for modified barium swallow study [abstract]. Arch Phys Med Rehabil. 1995;76:1040.
7. Widdicombe J G. Reflexes from the upper respiratory tract. Bethesda, Md.: The American Physiological Society; 1986.
8. Addington W R, Stephens R E, Gilliland K, Miller S P. Tartaric acid-induced cough and the superior laryngeal nerve evoked potential. Am J Phys Med Rehabil. 1998;77:523–6.
9. Sakamoto S, Fujimura M, Kamio Y, Saito M, Yasui M, Miyake Y, Matsuda T. [Relationship between cough threshold to inhaled tartaric acid and sex, smoking and atopy in humans]. Nihon Kyobu Shikkan Gakkai Zasshi. 1990;28:1478–81.
10. Fujimura M, Sakamoto S, Kamio Y, Matsuda T. Sex difference in the inhaled tartaric acid cough threshold in non-atopic healthy subjects. Thorax. 1990;45:633–4.
11. Tomori Z, Widdicombe J G. Muscular, bronchomotor and cardiovascular reflexes elicited by mechanical stimulation of the respiratory tract. J Physiol (Lond). 1969;200:25–49.
12. Sant'Ambrogio G, Widdicombe J. Reflexes from airway rapidly adapting receptors. Respir Physiol. 2001;125:33–45.
13. Addington W R, Stephens R E, Goulding R E. Anesthesia for the superior laryngeal nerves and tartaric acid-induced cough. Arch Phys Med Rehabil. 1999;80:1584–6.
14. Coleridge J C, Coleridge H M. Afferent vagal C fibre innervation of the lungs and airways and its functional significance. Rev Physiol Biochem Pharmacol. 1984;99:1–110.
15. Widdicombe J G. Afferent receptors in the airways and cough. Respir Physiol. 1998 October;114:5–15.
16. Widdicombe J. Airway receptors. Respir Physiol. 2001;125:3–15.
17. Widdicombe J G. Chemoreceptor control of airways. Respir Physiol. 1992 Mar;87:373–81.
18. Youtsey J W. Egan's Fundamentals of Respiratory Care. In: Egan D F, Scanlan C L, Spearman C B, Sheldon R L, eds. 5th/ed. St. Louis: Mosby; 1990:p. 387.

BACKGROUND OF THE INVENTION

The laryngeal cough reflex (LCR) and its precursor, the laryngeal cough expiratory reflex (LCER), are primal, brainstem mediated reflexes that have been shown in humans to protect the upper airway from the aspiration of potentially harmful material into the lungs. [1,2]

The LCER, when stimulated via the inhalation of a composition of tartaric acid, triggers a cascade of neurological events which ultimately results in the contraction of the abdominal and intercostal muscles to produce an initial expiration in an attempt to clear the abnormal aspirant. This is followed by a series of more forceful coughs with inspiratory and expiratory components (LCRs). [3]

There has been limited research performed on the use of inhaled tartaric acid to induce cough in asthmatic subjects. A study by Fujimura and coworkers showed that the cough threshold to tartaric acid did not differ between normal and asthmatic subjects and found that there was no correlation between cough threshold and bronchial responsiveness, supporting the hypothesis that cough and bronchoconstriction are separate airway reflexes. [4,5] No prior studies that we are aware of have fully described the effects of inhaled tartaric acid on the pulmonary function parameters in asthmatics.

Over the past seven years we have tested the LCER/LCR with nebulized compositions of tartaric acid (the reflex cough test, or RCT) to assess the integrity of the subjects' defensive mechanisms and thus to decide the appropriate treatment regime to avoid aspiration pneumonia in patients with cerebral damage. The RCT has also been performed in normal subjects and in patients with multiple co-morbidities, including asthma and COPD. [1,2,6] There have been no obvious adverse events related to this chemoirritant, and we therefore expected that pulmonary function parameters would not significantly change in either the normal or an asthmatic group after inhalation of the tartaric acid composition. However, laryngeal irritation is known to cause reflex bronchoconstriction, mucosal vasodilatation and excess mucus secretion. [7] Accordingly, one would expect the mechanical effects of the first two but not the last to subside quickly. In addition, the violent respiratory movements of coughing could perturb airway function. Thus, there is the potential for adverse changes as the result of tartaric acid inhalation, and we theorized that these might be detected through pulmonary function tests (PFT).

The original intent of this investigation, therefore, was to determine parameters fo use of objective PFTs in examining the effects of tartaric acid-induced cough on pulmonary function in normal healthy and asthmatic individuals. Outcome measures included specific pulmonary functions, and the occurrence of airway obstruction or bronchospasm.

SUMMARY OF THE INVENTION

With the foregoing in mind, the present invention advantageously provides a nebulizer apparatus for treatment of a patient having a pulmonary disease involving chronic obstruction of the airways. The apparatus is adapted for self-treatment by the patient, and comprises a container sized to be portable by the patient and having therein a chamber containing a composition comprising a pharmaceutically acceptable carrier mixed with L-tartaric acid. A nebulizing valve having an opening connected to the chamber is positioned so as to provide an outlet therefor, and a source of motivating force connected with the chamber so as to motivate the composition through the opening in the nebulizing valve to thereby cause nebulization of the composition. In the apparatus, nebulization comprises droplets having an airborne diameter of less than about 10 $\mu$m, and the L-tartaric acid is mixed in the composition in an amount effective for causing an increase in peak respiratory flow when inhaled by the patient.

The invention also includes a method for treatment of a patient having a pulmonary disease involving chronic obstruction of the airways. The method comprises inhalation by the patient of a nebulized composition comprising a pharmaceutically acceptable carrier mixed with L-tartaric acid in an amount effective for causing an increase in peak respiratory flow. The pharmaceutically acceptable carrier preferably comprises a solution having at least about 0.15 M sodium chloride, and at least about 20% L-tartrate.

A treatment kit is adapted for self-treatment by a patient having a pulmonary disease involving chronic obstruction of the airways. The kit comprises a container sized to be portable by the patient, and containing a pharmaceutically acceptable carrier mixed with L-tartaric acid in an amount effective for causing an increase in peak respiratory flow when inhaled by the patient, a nebulizing valve connected to the chamber, and a source of pneumatic pressure to motivate the composition through the valve to thereby generate a nebulized composition comprising droplets having an airborne diameter of less than about 10 $\mu$m. The kit also includes a generally tubular mouthpiece connectable to the container so as to be in fluid connection with the nebulizing valve to convey the nebulized composition into a patient's mouth for oral inhalation by the patient. Optionally, the kit may also comprise a removable cap fitting over the mouthpiece, a nose clip to aid the patient in oral inhalation of the composition, and a respiratory flow meter for determining increase in peak respiratory flow.

BRIEF DESCRIPTION OF THE DRAWINGS

Some of the features, advantages, and benefits of the present invention having been stated, others will become apparent as the description proceeds when taken in conjunction with the accompanying drawings in which.

DETAILED DESCRIPTION OF THE PREFERRED EMBODIMENT

Figure 1:
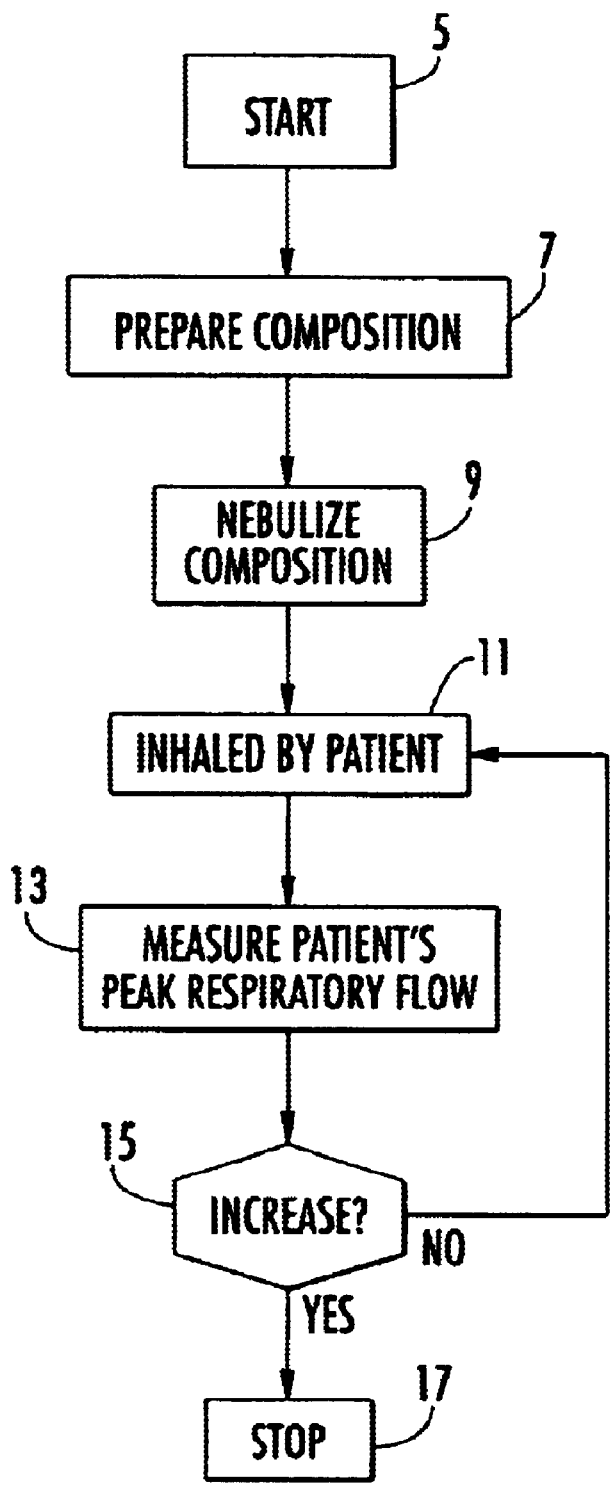
FIG. 1 is a flow diagram illustrating a treatment method according to an embodiment of the present invention.
Figure 2:
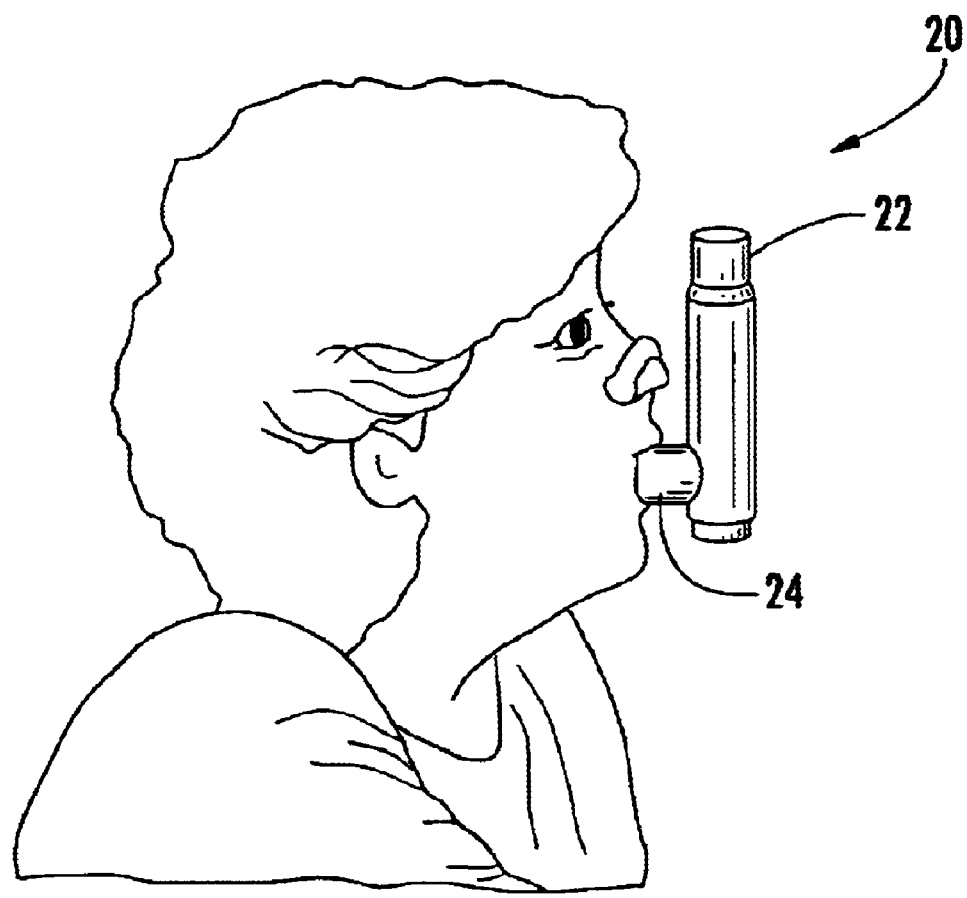
FIG. 2 shows the nebulizer apparatus of the present invention in use.
Figure 3:
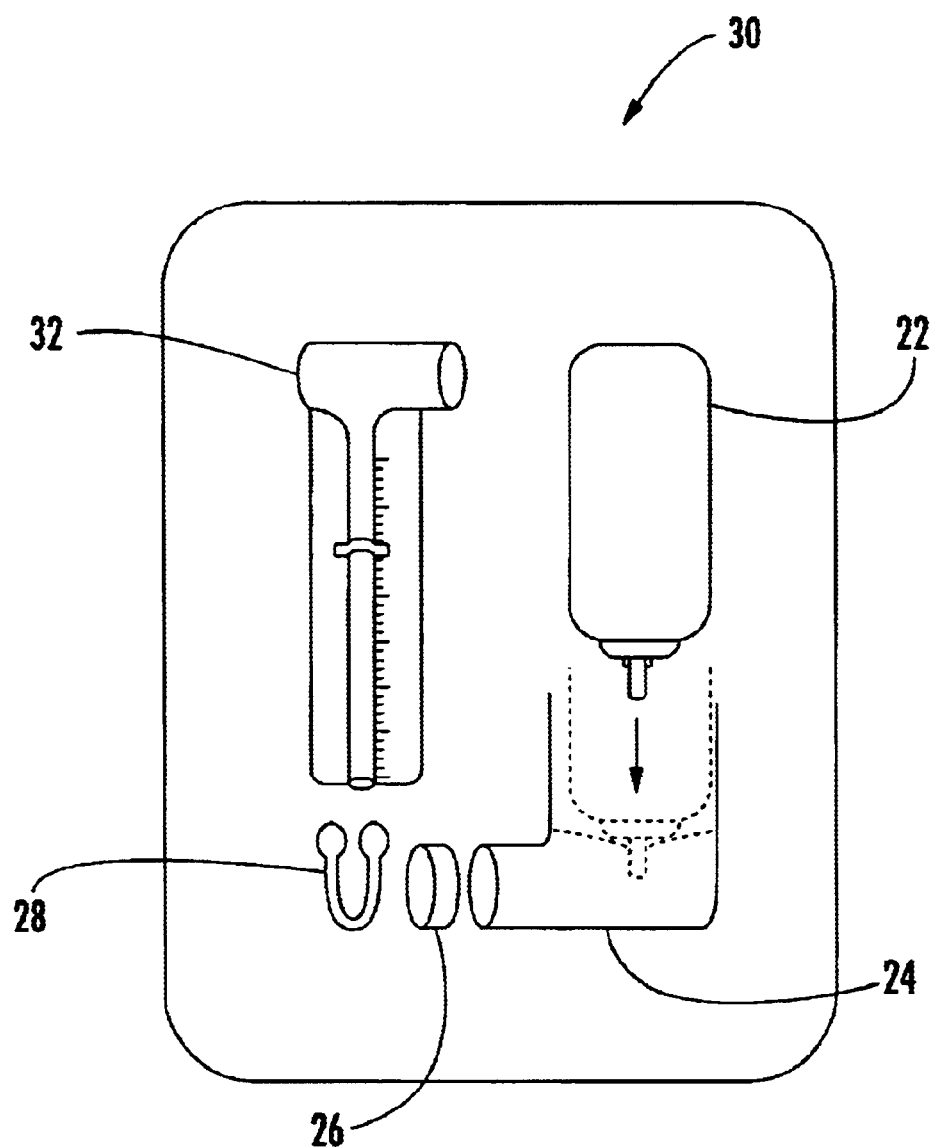
FIG. 3 is a top plan view of a kit comprising the described invention for self-treatment by a patient.

The present invention will now be described more fully hereinafter with reference to the accompanying drawings, in which preferred embodiments of the invention are shown. This invention may, however, be embodied in many different forms and should not be construed as limited to the illustrated embodiments set forth herein. Rather, these illustrated embodiments are provided so that this disclosure will be thorough and complete, and will fully convey the scope of the invention to those skilled in the art.

Study Subjects

After informed consent and health history interviews, 20 healthy and 20 asymptomatic, medicated asthmatic volunteers engaged in a two-part evaluation of PFT. All forty subjects were non-smokers. The study was performed in a physician's office. A certified respiratory therapist administered the RCT and performed all the PFTs.

Study Design

The RCT stimulates cough receptors in the vestibule of the larynx and initiates the LCER/LCR.[4,5,8–10] The RCT (Pneumoflex Systems, Inc., Orlando, Fla.) was performed by administering to the subjects a composition comprising a 20% solution of pharmaceutical grade L-tartaric acid dissolved in sterile 0.15 M NaCl solution, and inhaled from a Bennett Twin nebulizer. During the inhalation, the subject's nose was pinched closed. The nebulizer output was approximately 0.2 ml/min.[1,2,4–6,8,10] The subjects were tested in the standing position for all PFT and RCT tests. Subjects were tested for two effective inhalations. The subject was asked to exhale, then insert the mouthpiece, and take a sharp, deep inhalation. Leakage around the mouthpiece and "puffing" the nebulizer were not considered effective inhalations. The respiratory therapist used a Spiromate AS-600 for all PFTs (SN6546, Riko Medical and Scientific Corporation Instruments).

In the first part of the evaluation a baseline PFT was performed, followed by two separate inhalations of a nebulized solution of 20% tartaric acid. In the second part, the PFT was repeated 5 min after the second inhalation. After the RCT, each subject answered questions regarding the effects and sensations experienced during inhalation. Subjects were monitored and questioned for residual effects for 15 min after the procedure. A 24 h follow up interview was conducted regarding the experience of the procedure.

Five specific pulmonary variables were examined, both before and after administration of the RCT, included:

| | |
|---|---|
| $FEV1_{(Pre-RCT)}$ | Forced Expiratory Volume in 1 s before the RCT |
| $FEV1_{(Post-5\ RCT)}$ | Forced Expiratory Volume in 1 s 5 min after the RCT |
| $FVC_{(Pre-RCT)}$ | Forced Vital Capacity before the RCT |
| $FVC_{(Post-5\ RCT)}$ | Forced Vital Capacity 5 min after the RCT |
| $FEV1/FVC_{(Pre-RCT)}$ | FEV1/observed FVC before the RCT |
| $FEV1/FVC_{(Post-5\ RCT)}$ | FEV1/observed FVC 5 min after the RCT |
| $PIF_{(Pre-RCT)}$ | Peak Inspiratory Force before the RCT |
| $PIF_{(Post-5\ RCT)}$ | Peak Inspiratory Force 5 min after the RCT |
| $PEF_{(Pre-RCT)}$ | Peak Expiratory Force before the RCT |
| $PEF_{(Post-5\ RCT)}$ | Peak Expiratory Force 5 min after the RCT |

Analysis

Data collection was conducted on each subject and included informed consent, health history questionnaire, and a pulmonary function data printout. Twenty normal and twenty asthmatic subjects were selected for determining statistical differences between pre and post PFT variables. Both test groups had 10 males and 10 females. The mean age was calculated for each group. Two nonparametric techniques are used according to the magnitude of skewness, which was determined by comparing $g=k/s$ with the critical value at $\alpha=0.05$, where $$k = \frac{n\sum (x_i - \bar{x})^3}{(n-1)(n-2)}, \text{ and } s = \left(\frac{\sum_{}^{n}(x_i - \bar{x})^2}{n-1}\right)^{1/2}.$$

At $\alpha=0.05$ the two-sided critical value is 0.942 for n=20. If g>0.942 then skewness is significant. A positive value for g>0 means there is positive skewness (Median<Mean). Differences that are significantly skewed were examined by using the sign test. However, differences that were not significantly skewed were examined by using a more powerful technique the Wilcoxon Signed Rank Test.

Results

The mean age of the normal and asthmatic subjects was 36.85±8.62 (S.D.), and 66.20±13.13, respectively. All subjects had a normal reflex response to RCT, consisting of LCER efforts followed by the LCR without adverse effects.

A. Statistical Comparison for Normal Subjects

The statistics for skewness are displayed in Table 1. Five paired comparisons were investigated. Shown in Table 1 are the appropriate statistical tests and the corresponding P values; PIF(Pre-RCT) is significantly smaller than PIF$_{(Post-5\ RCT)}$, by about 21%.

B. Statistical Comparison for Asthma Subjects

The statistics for skewness are shown in Table 2. Five paired comparisons were investigated. Also shown are the appropriate statistical tests and the corresponding P values; PEF$_{(Pre-RCT)}$ is significantly smaller than PEF$_{(Post-5\ RCT)}$, by about 7%.

C. Comparison Between Asthma Data and Normal Data

Table 3 shows that for each of the ten investigated variables, the normal group always had greater mean values than did the asthma group.

TABLE 1

Skewness Statistics and Non Parametric Comparisons for Normal Subjects

| Differences | Skewness Statistics | Skewed or Symmetric | Statistical Test | P-Value |
|---|---|---|---|---|
| FEV1$_{(Pre-RCT)}$ - FEV1$_{(Post-5\ RCT)}$ | +2.510 | Skewed | Sign test | .359 |
| FVC$_{(Pre-RCT)}$ - FVC$_{(Post-5\ RCT)}$ | +1.973 | Skewed | Sign test | .648 |
| FEV1/FVC$_{(Pre-RCT)}$ - FEV1/FVC$_{(Post-5\ RCT)}$ | +3.808 | Skewed | Sign test | .503 |
| PIF$_{(Pre-RCT)}$ - PIF$_{(Post-5\ RCT)}$ | -.204 | Symmetric | Wilcoxon | .004 |
| PEF$_{(Pre-RCT)}$ - PEF$_{(Post-5\ RCT)}$ | +1.046 | Skewed | Sign test | .824 |

TABLE 2

Skewness Statistics and Non Parametric Comparisons for Asthma Subjects

| Differences | Skewness Statistics | Skewed or Symmetric | Statistical Test | P value |
|---|---|---|---|---|
| FEV1$_{(Pre-RCT)}$ - FEV1$_{(Post-5\ RCT)}$ | +.143 | Symmetric | Wilcoxon | .198 |
| FVC$_{(Pre-RCT)}$ - FVC$_{(Post-5\ RCT)}$ | +.976 | Skewed | Sign test | .503 |
| FEV1/FVC$_{(Pre-RCT)}$ - FEV1/FVC$_{(Post-5\ RCT)}$ | -3.232 | Skewed | Sign test | .503 |
| PIF$_{(Pre-RCT)}$ - PIF$_{(Post-5\ RCT)}$ | -1.202 | Skewed | Sign test | .210 |
| PEF$_{(Pre-RCT)}$ - PEF$_{(Post-5\ RCT)}$ | -.023 | Symmetric | Wilcoxon | .014 |

TABLE 3

Descriptive Comparison between Normal and Asthma Subjects

| Variables | Mean (Normal) | Standard Deviation (Normal) | Mean (Asthma) | Standard Deviation (Asthma) |
|---|---|---|---|---|
| FEV1$_{(Pre-RCT)}$ | 3.99 | .74 | 1.98 | .820 |
| FEV1$_{(Post-5\ RCT)}$ | 3.88 | .77 | 2.07 | .653 |
| FVC$_{(Pre-RCT)}$ | 4.93 | .94 | 2.92 | 1.06 |
| FVC$_{(Post-5\ RCT)}$ | 4.87 | 1.01 | 2.97 | 1.04 |
| FEV1/FVC$_{(Pre-RCT)}$ | 81.18 | 5.77 | 67.39 | 19.70 |
| FEV1/FVC$_{(Post-5\ RCT)}$ | 75.60 | 19.00 | 74.00 | 17.70 |
| PIF$_{(Pre-RCT)}$ | 5.26 | 1.79 | 2.79 | 1.09 |
| PIF$_{(Post-5\ RCT)}$ | 6.38 | 2.05 | 3.24 | 1.62 |
| PEF$_{(Pre-RCT)}$ | 7.83 | 2.20 | 3.67 | 1.98 |
| PEF$_{(Post-5\ RCT)}$ | 7.65 | 1.95 | 4.03 | 2.24 |

Discussion

There was no significant decrease in either the normal or asthmatic pulmonary function parameters after inhalation of tartaric acid. This supported our expectation that RCT does not have adverse effects, in spite of the potential increases in bronchomuscular tone, mucosal vasodilatation and lower airway mucus secretion. Since these last three changes are almost invariably produced by irritant-induced reflexes from the laryngeal mucosa [7], it is unlikely that a direct reflex from the laryngeal region can explain the increases in peak inspiratory and expiratory flows. Mechanical irritation of the nasopharyngeal mucosa causes bronchodilatation [11], but the receptors for this reflex are not very chemosensitive and the associated respiratory changes are not expiration or cough but are inspiratory efforts (the aspiration reflex). Based on this, it would appear that nasopharyngeal reflexes are unlikely to mediate any bronchodilatation after the RCT.

The laryngeal receptors for the LCER and the LCR are almost certainly rapidly adapting ("irritant") receptors (RARs), both in experimental animals [12] and in man [8], and they are stimulated by acid solutions. C-fiber receptors in the trachea, bronchi and alveolar walls are also all stimulated by acid solutions, and while the response of laryngeal C-fiber receptors to acid does not seem to have been studied, there is no reason to believe that they behave differently from those elsewhere in the respiratory tract. In humans, however, bilateral anesthesia of the internal branch of the superior laryngeal nerve abolishes tartaric acid induced cough and permits tidal breathing of the nebulized vapor without coughing-supporting the proposition that the RARs are responsible for laryngeal cough.[13] By contrast, stimulation of C-fiber receptors in the lower respiratory tract causes apnea or rapid shallow breathing, bronchoconstriction, mucus secretion and mucosal vasodilatation by central nervous reflexes [14,15] and, for the airway changes by local release of sensory neuropeptides such as substance P [16]. These responses are not consistent with the increases in peak respiratory flows described here. Thus, it is difficult to ascribe the unexpected increases in peak flow to known neurological mechanisms.

One possibility is that the strong mechanical events triggered by laryngeal coughing could be responsible for the increases in peak flow. Large lung inflations would stretch the airways and might open any collapsed airways. In the asthmatics, if any mucus is present in the airways, coughing might remove it and thereby increase airway caliber. The hyperventilation of coughing might cause bronchodilatation, since hypercapnia and hypoxia are stimulants to bronchoconstriction.[17] A further possibility is that the pronounced cardiovascular changes associated with cough might include a release of catecholamines from the adrenal glands, which could have quite a long-lasting bronchodilator effect.

We cannot explain the unexpected result wherein the healthy subjects demonstrated an RCT showing increased peak inspiratory flow, whereas in the asthmatics it was peak expiratory flow that increased. Possibly the considerable differences in mean age and in pulmonary function parameters between the two groups (Table 3) may be a factor. While peak flow measurements may be influenced by subject cooperation and effort, no lack of cooperation was apparent in these subjects.[18]

Accordingly, we conclude that the RCT causes no adverse changes in pulmonary function parameters, but rather unexpectedly brings about an enhancement of peak respiratory flow in both normal subjects and in asthmatics by an unknown mechanism.

Preferred Embodiments of the Invention.

With the foregoing in mind, the invention includes a method for treatment of a patient having a pulmonary disease involving chronic obstruction of the airways. The method comprises inhalation of a nebulized composition of L-tartrate in a pharmaceutically acceptable carrier in an amount effective for causing an increase in peak respiratory flow. As shown in FIG. 1, the method starts [Block 5] with preparation of the composition [Block 7], followed by nebulization of the composition [Block 9], inhalation of the nebulized composition by the patient [Block 11], and finally by measuring the respiratory peak flow [Block 13]. Inhalation may be repeated if no increase is measured [Block 15]. If increased flow is noted, the method stops [Block 17]. As noted above, inhalation of L-tartrate will cause the patient to cough, however, it is not known whether the cough mechanism is instrumental in producing the discovered increase in peak respiratory flow following the treatment. The L-tartrate is preferably in a substantially soluble form in an aqueous solution of isotonic sodium chloride. A concentration of L-tartrate which is preferred in the present invention is about 20% L-tartrate.

The skilled will appreciate that the nebulized composition preferably comprises droplets having an airborne diameter of about 10 $\mu$m or less to promote penetration into the lower respiratory airways. The composition was found to be adequately nebulized at a rate of about 0.2 ml per minute. In the present invention, the pulmonary disease comprises the group of chronic obstructive pulmonary diseases consisting of simple chronic bronchitis, asthma and asthmatic bronchitis, chronic obstructive bronchitis, emphysema, bronchiectasis, cystic fibrosis, and bronchiolitis.

Another aspect of the invention includes a nebulizer apparatus 20 adapted for self-treatment by a patient having a pulmonary disease involving chronic obstruction of the airways, as shown in use in FIG. 2. The nebulizer includes a container 22 sized to be portable by the patient and having therein a chamber containing a composition comprising a pharmaceutically acceptable carrier mixed with L-tartaric acid in an amount effective for causing an increase in peak respiratory flow when inhaled by the patient. As known in the art, a nebulizing valve having an opening is connected to the chamber so as to provide an outlet therefor. A source of motivating force communicates with the chamber so as to motivate the composition through the opening in the nebulizing valve to thereby cause nebulization of the composition to comprise droplets having an airborne diameter of less than about 10 $\mu$m. Typically, the container 22 comprises a metal cylinder, and the source of motivating force comprises pneumatic pressure, and preferably a compressed gas within the container. Additionally, the nebulizer apparatus 20 comprises a mouthpiece 24 positioned in fluid connection with the opening and downstream therefrom to thereby convey the nebulized composition to the mouth of the patient so as to facilitate oral inhalation. The pharmaceutically acceptable carrier preferably comprises a solution of at least about 0.15 M sodium chloride, and is prepared with at least about 20% L-tartaric acid.

Yet another aspect of the invention, as shown in FIG. 3, includes a treatment kit 30 adapted for self-treatment by a patient having a pulmonary disease involving chronic obstruction of the airways. The kit 30 comprises the container 22 described above, and a mouthpiece 24 connectable to the container so as to be in fluid connection with the valve opening and downstream therefrom to thereby convey the nebulized composition into a patient's mouth to facilitate oral inhalation. The treatment kit advantageously may further comprise a removable cap 26 fitting over the mouthpiece 24 for protection. Moreover, the treatment kit may include a plurality of containers thereby providing replacements, and may also include a nose clip 28, and a respiratory flow meter 32 for measuring increased peak respiratory flow.

Accordingly, the specification discloses a typical preferred embodiment of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

That which is claimed:

1. A method for treatment of a patient having a pulmonary disease involving chronic obstruction of the airways, the method comprising inhalation by the patient of a nebulized composition comprising a pharmaceutically acceptable carrier mixed with L-tartaric acid in an amount effective for causing an increase in peak respiratory flow.

2. The method of claim 1, wherein the pharmaceutically acceptable carrier comprises an aqueous solution and the L-tartaric acid is substantially soluble therein, thereby forming an L-tartrate.

3. The method of claim 1, wherein the pharmaceutically acceptable carrier comprises a solution of sodium chloride.

4. The method of claim 1, wherein the pharmaceutically acceptable carrier comprises a solution having at least about 0.15 M sodium chloride.

5. The method of claim 1, wherein the composition comprises at least about 20% L-tartrate.

6. The method of claim 1, wherein the nebulized composition comprises droplets having an airborne diameter of about 10 $\mu$m or less.

7. The method of claim 1, wherein the composition is nebulized at a rate of about 0.2 ml per minute.

8. The method of claim 1, wherein the pulmonary disease is selected from the group of chronic obstructive pulmonary diseases consisting of simple chronic bronchitis, asthma and asthmatic bronchitis, chronic obstructive bronchitis, emphysema, bronchiectasis, cystic fibrosis, and bronchiolitis.

* * * * *